United States Patent [19]

Söderkvist

[11] Patent Number: 4,532,838

[45] Date of Patent: Aug. 6, 1985

[54] METHOD IN A MICROTOME FOR CREATING THE POSSIBILITY THAT THE SLIT BETWEEN THE KNIFE EDGE AND THE SPECIMEN CAN BE MADE EXTREMELY NARROW

[75] Inventor: Anton Söderkvist, Vällingby, Sweden

[73] Assignee: LKB-Produkter AB, Bromma, Sweden

[21] Appl. No.: 505,200

[22] Filed: Jun. 17, 1983

[30] Foreign Application Priority Data

Jun. 28, 1982 [CH] Switzerland ............... 8203967

[51] Int. Cl.³ ............................................. G01N 1/06
[52] U.S. Cl. ........................................ 83/13; 83/521; 83/915.5
[58] Field of Search .................... 83/13, 915.5, 521; 33/189, 185, 186

[56] References Cited

U.S. PATENT DOCUMENTS

| | | | |
|---|---|---|---|
| 3,377,898 | 4/1968 | Persson | 83/521 X |
| 3,599,523 | 8/1971 | Pickett | 83/915.5 X |
| 3,845,659 | 11/1974 | Wikefeldt et al. | 83/915.5 X |
| 4,403,860 | 9/1983 | Pryor | 33/185 R X |

FOREIGN PATENT DOCUMENTS 7504111 2/1976 Sweden .

*Primary Examiner*—Frank T. Yost
*Attorney, Agent, or Firm*—Fisher, Christen & Sabol

[57] ABSTRACT

Method in a microtome, especially an ultramicrotome, in which a knife edge, turnable around its longitudinal axis, is used to cut sections from a specimen by making the specimen downwardly pass over the knife edge. The distance between the knife edge and the specimen before cutting is made extremely narrow without the specimen touching the knife. The slit is lit up from below by a light waveguide, one end of which is located under the knife edge and is turned with this and the other end of which is lit up by a light source movable in relation to the turning of the knife edge. The light from the waveguide is reflected against the surfaces of the knife as well as of the specimen which are turned towards the slit. The image of the knife surface reflected in the specimen surface, the size of which is proportional to the breadth of the slit, is viewed from at least one point located in a vertical plane outside of the vertical plane of the slit and on the same side of this as the knife.

6 Claims, 2 Drawing Figures

METHOD IN A MICROTOME FOR CREATING THE POSSIBILITY THAT THE SLIT BETWEEN THE KNIFE EDGE AND THE SPECIMEN CAN BE MADE EXTREMELY NARROW

BACKGROUND OF THE INVENTION

1. Field of the Invention

The invention refers to a method in a microtome, especially an ultramicrotome, in which a knife edge which can be oriented around its longitudinal axis, is used to cut sections from a specimen by making the specimen pass downwardly over the knife edge, thereby making it the distance between the knife edge and the specimen before cutting extremely narrow without the specimen touching the knife.

2. Prior Art

Within microtomy, especially ultramicrotomy, there is a strong requirement for the monitoring and controlling the approach of the cutting knife to the specimen from which the sections are to be cut. The knives used generally consist of glass or diamond and the knife edges are extremely sharp and, therefore, are easy to damage if the knife, when approaching the specimen comes into contact with the specimen or if the first cut is too thick. On the other hand, if due to insufficient sensitivity of the control of the distance between the knife and the specimen surface, one is forced to feed the knife and the specimen in very small steps at a long distance between the knife and the specimen the process will take an unreasonable amount of time. According to an earlier known method, the approach between the knife and the specimen block is carried out in such a way that the slit between the knife and the specimen block is lit up from below by a separate lamp located in the knife holder under the specimen block and the knife. According to another method described in Swedish Pat. No. 7504111-1, the knife is lit up from below via a mirror. This latter method can, however, only be used for glass knives. In the former method the location of the light source under the knife holder leads to thermal disturbances and furthermore, a light beam which is too strong and too broad is obtained. This gives a dazzling effect which is especially disturbing in the subsequent cutting procedure in which so-called diffused light is used. In order to reduce the thermal disturbances and to decrease the dazzling effect, the lamp could be replaced by a fiber optic arrangement placed on the knife holder. The drawback is, however, that one has to take away the fiber cable before the cutting is started which easily gives rise to mechanical disturbances of the knife holder. Or, one has to let the cable remain during the cutting, which easily gives rise to mechanical tensions between the knife stage and the base plate and which, furthermore, contributes to the transfer of vibrations to the knife holder.

BROAD DESCRIPTION OF THE INVENTION

The object of the invention is, therefore, to provide a method in which the above mentioned disadvantages are eliminated and which is applicable to glass knives as well as to diamond knives.

The invention involves a method in which a microtome, especially an ultramicrotome, wherein a knife edge is turnable around its longitudinal axis, is used to cut sections from a specimen by making the specimen pass the knife edge downwards, in order to make it possible that the distance between the knife edge and the specimen before cutting can be made extremely narrow without the specimen touching the knife. The slit is lit up from below by a light waveguide, one end of which is located under the knife edge and is turned with this, and the other end of which is lit up by a light source movable in relation to the turning of the knife edge. The light from the waveguide then reflects against the surfaces of the knife as well as of the specimen which is turned towards the slit. The image of the knife surface is reflected in the specimen surface. The size of the image is proportional to the breadth of the slit. The specimen is looked at from at least one point located in a vertical plane outside of the vertical plane of the slit and on the same side of this as the knife.

DETAILED DESCRIPTION OF THE INVENTION

Figure 1:
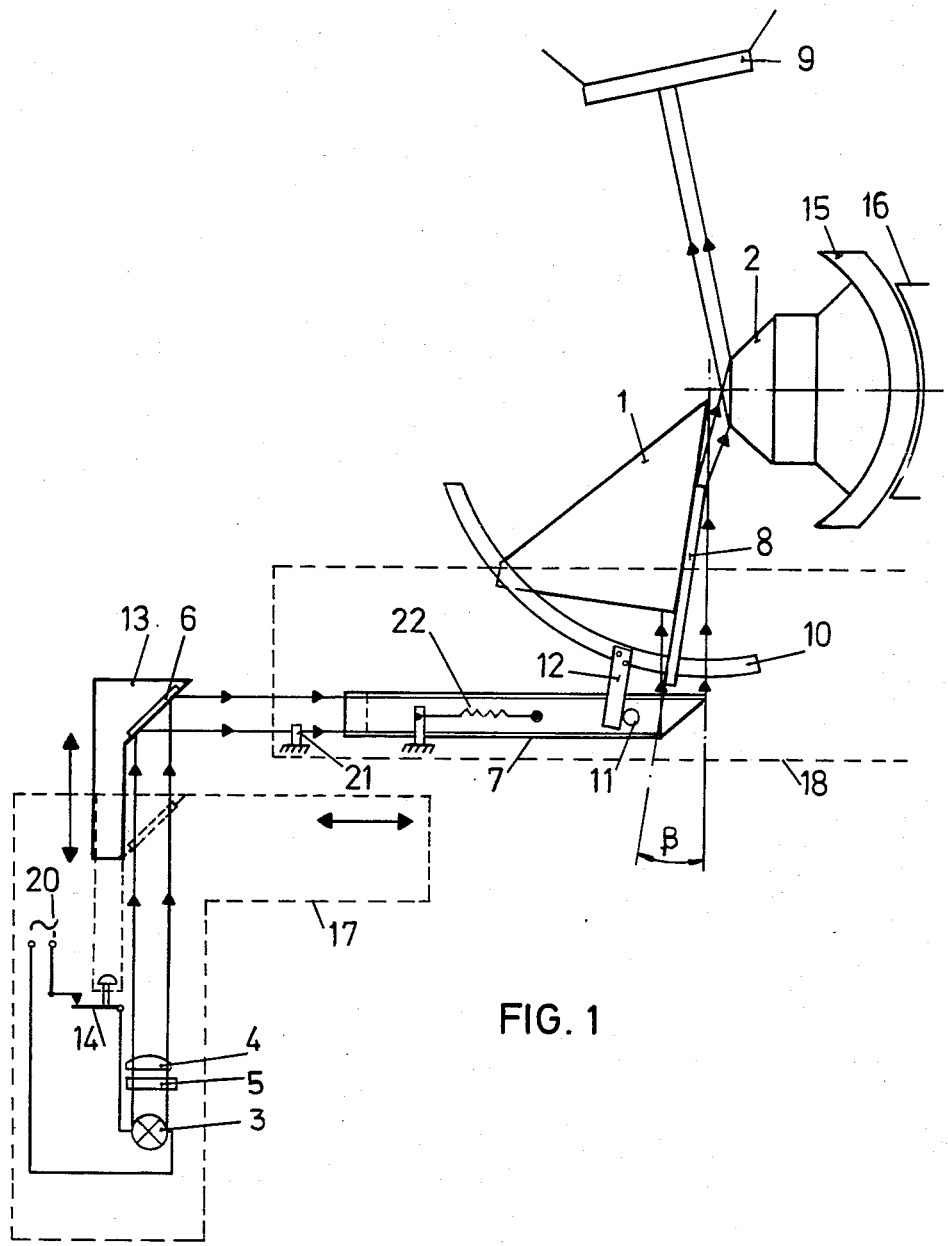
Figure 2:
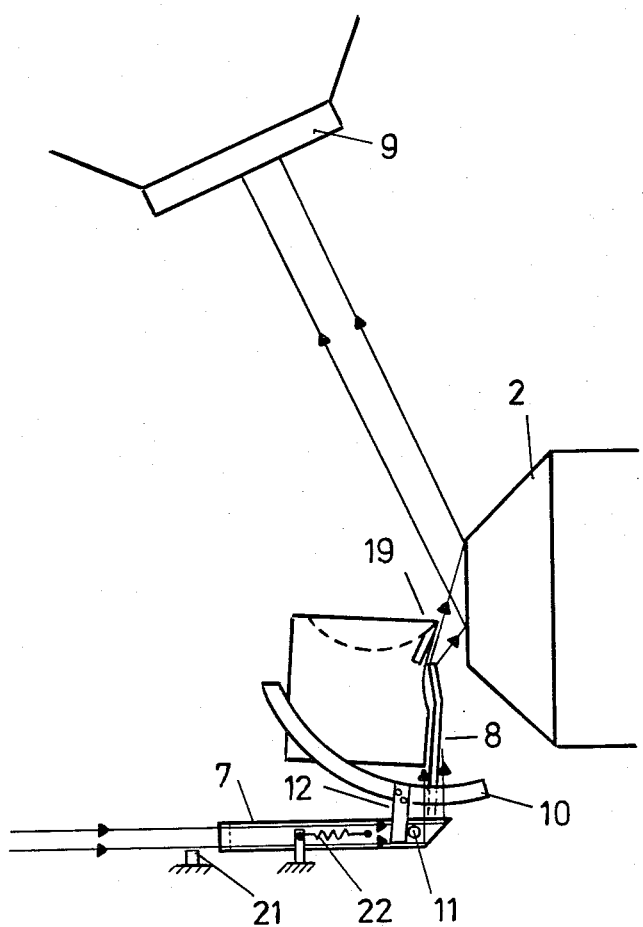

The invention is now explained in detail, with reference being made to the enclosed drawings in which:

FIG. 1 is a schematic of an ultramicrotome provided with an optical arrangement for carrying out the invention when using a glass knife; and FIG. 2 is a view showing the part of the device according to FIG. 1 where the glass knife has been replaced by a diamond knife.

In FIG. 1, which schematically shows a side-view of ultramicrotome, reference numeral 1 denotes a glass knife located in a knife holder and reference numeral 2 denotes a specimen designed as a truncated pyramid. The specimen is fixed in a conventional way in torsional bow 15 which is supported by specimen arm 16. Knife holder 1 is placed in cradle 10 so that knife 1 can be turned around the axis of the knife edge in order to provide different so-called clearance angles $\beta$, which is the angle between the vertical front surface of the specimen and the plane of the knife facet which is turned towards the specimen.

Reference numeral 3 denotes a filament bulb which via lens 4 and heat absorbing filter 5 lights up plane mirror 6 from which the light is reflected against light waveguide prism 7. Mirror 6 is placed in mirror holder 13, which is designed as a slide, and built-in a frame 17, which also holds up microscope 9 of the ultramicrotome. As mirror holder 13 is brought to its upper end position lamp 3 is connected to voltage source 20 via switch 14. From mirror 6 the light is reflected against waveguide prism 7, in the opposite end of which the light beam is refracted upward and strikes light waveguide 8 at its lower edge. Via light waveguide 8 the light is conducted up toward the upper surface of the waveguide and strikes the very smooth and bright surface and the upper part of the knife at such angles that light reflections are obtained in microscope 9. The optical axis of microscope 9 leans in proportion to the specimen surface, so that the specimen surface functions as a mirror in which, except for the upper end of light waveguide 8, the upper part of the knife can be seen. This makes the whole specimen surface perceived as shining strongly when the knife is located relatively far from the specimen surface. Due to the fact that the light shines in towards the knife and the specimen similarly from a plane surface, the reflections are obtained in both beam paths when using a stereomicroscope. Furthermore, the location of the light source and the mirror holder in the frame of the movable microscope stand, as described above, means that the frame can be pushed freely toward or from the operator to the most suitable position for observation without the light intensity being changed in the light waveguides.

When the knife approaches the specimen surface the shining part is limited more and more by the very outermost border line of the knife edge and gradually forms a narrow line when the knife edge is brought to pass very close to the specimen surface. At a distance of about 1 μm the color tints appear which are characteristic when the slit between the knife edge and the specimen surface through which the light is to pass becomes smaller than the wavelength of the light used. After further feeding, the light completely dies away and the specimen can be brought into its up and down cutting movement combined with a suitable feeding step between each cutting movement. After a few cutting movements, contact is obtained between the knife and the specimen and the cutting of sections starts.

In waveguide prism 7 there is pin 11 and in cradle 10 there is located carrier 12, by means of which prism 7 of the cradle can be brought away from its left end position against which it is fixed by means of stop 21 and spring 22. Waveguide prism 7 is focused in such a way that the rear, left limitation line of the lit up field comes approximately in line with the rear plane of waveguide 8, when $\beta=0$. When the cradle is turned in such a way that the clearance angle increases, waveguide prism 7 is forced to follow, which results in the lower end of the waveguide 8 being equally lit up at all of the present values of the relief angle. At the same time the strongly shining front upper side of the prism giving disturbing side reflections in the microscope at great values of the clearance angle, is avoided, which is not the case if the light source is fixed. Furthermore, a good so-called dark field background is provided, i.e., the area under and on the sides of the specimen block remains dark irrespective of the value of the angle of clearance and, therefore, a maximum contrast between reflection and background is obtained.

The above mentioned focusing of light waveguide 7 allows its front peak to bulge out in front of the base of the knife holder cradle enough to give light directly to the specimen surface without the assistance of waveguide 8. The cradle is set in such a way that the angle of clearance is approximately as large as the angle of the microscope axis towards the specimen surface. Thus, a reflection is obtained in the microscope directly from the peak of waveguide 7 via the specimen surface. According to the description above, carrier 12 is designed in such a way that the waveguide stops in a pre-determined end position even if the value of the angle of clearance is further increased or if the cradle is completely taken away from its slide. This end position, determined by stop 21, is possible to trim so that errors of tolerance of the microscope angle and the location of the knife stage can be eliminated. By means of this arrangement the very important basic adjustment of the vertical orientation of the specimen surface is simplified. Especially, when having very small specimen block faces (sizes of 0.3×0.3 mm), it is very difficult to adjust the vertical orientation of the surface so that it catches the reflection desired when the knife approaches the surface if orientation bow 15 of the specimen is not suitably set. Locating the knife edge at a distance of about 0.5 to 1 mm from the specimen surface and with the specimen arm fixed in a horizontal position, the bow is adjusted until an optimal reflection is obtained in the microscope from the specimen surface, which means that the surface is vertical. The knife holder cradle can then be set at a value (usually lower) for the relief angle for cutting and the knife can be brought closer to the specimen by means of the reflection which then substantially comes from waveguide 8. Finally, the end of the waveguide prism 7 which is turned towards the mirror 6 can be provided with a concave end surface in the horizontal plane so that the knife holder cradle can be turned at least ±10° in the horizontal plane without shadings arising. This is necessary in the cases where the front surface of the specimen block does not subtend at a right angle with its symmetry line.

In FIG. 2 a part of the ultramicrotome described in FIG. 1 is shown, in which glass knife 1 has been replaced by a diamond knife and holder 19 belonging to it. As to the rest of the device, the same reference numeral are used as in FIG. 1. Diamond knives are generally fixed in metal frames and then the edge facet often has an angle which is disadvantageous to the generation of suitable light reflections at the approach of the knife to the specimen. This is especially valid when the diamond knife is refaced after having been damaged. This means that the reflection surfaces obtained by the use of a diamond knife edge facet have quite variable angles as compared to when glass knives are used, the facet surface of which, turned towards the specimen is always vertical at an angle of clearance of 0°. When using diamond knives the light waveguide is, therefore, bent in an angle of about 5° which brings it into the cavity wherein the diamond is embedded. The light falls then from the upper end of the light guide towards the surface of the specimen in such angles that a good reflection from this surface is obtained in the microscope. In order to enable the use of a glass knife and a diamond knife, alternatively, without the exchange of the waveguide 8, waveguide 8 is formed of flexible plastic which permits straightening out the above mentioned angle of 5° in the case of a glass knife waveguide 8 returns to its original position when a diamond knife is again inserted.

We claim:

1. A method for cutting sections from a specimen using a microtome, said microtome comprising:
   a specimen holder;
   a knife having a knife edge, said knife being turnable about said knife edge as an axis, said knife having a front surface facing said specimen holder;
   drive means for moving said specimen holder and said knife edge toward one another, and for moving said specimen holder downwardly relative to said knife edge;
   a light waveguide having one end disposed below said knife edge and arranged to direct light passing therethrough on to a portion of said front face of said knife adjacent said knife edge, said one end of said light waveguide being arranged to turn with said knife about said knife edge as axis; and
a light source for supplying light to the opposed end of said light waveguide, said light source being arranged to move with said opposed end of said light waveguide as said light waveguide is turned about said knife edge as axis,
said method comprising:
mounting said specimen in said specimen holder;
bringing said knife edge adjacent said specimen mounted in said specimen holder, thereby forming a slit between said knife edge and said specimen;
passing light from said light source through said light waveguide, thereby causing said light to impinge upon said front face of said knife, and at least part of said impinging light to be reflected from said front face of said knife on to said specimen, thereby forming on said specimen an illuminated area which, when viewed from a point lying above said knife edge and on the opposed side of the vertical plane containing the knife edge from the specimen holder, has a breadth proportional to the width of the slit;

bringing said knife edge and said mounted specimen closer together, thereby reducing the width of said slit, while observing said illuminated area from said point to ensure that said knife edge does not contact said mounted specimen; and activating said drive means, thereby moving said specimen holder and said knife edge toward one another, and moving said specimen holder downwardly relative to said knife edge, and causing said knife to cut sections from said mounted specimen.

2. A method according to claim 1 wherein said reduction of the width of said slit is continued at least until color tints appear in said slit, thereby indicating that the width of said slit is less than the wavelength of said light passing through said light waveguide.

3. A microtome apparatus comprising:

a specimen holder;

a knife having a knife edge, said knife being turnable about said knife edge as an axis, said knife having a front surface facing said specimen holder;

drive means for moving said specimen holder and said knife edge toward one another, and for moving said specimen holder downwardly relative to said knife edge;

a light waveguide having one end disposed below said knife edge and arranged to direct light passing therethrough on to a portion of said front face of said knife adjacent said knife edge, said one end of said light waveguide being arranged to turn with said knife about said knife edge as axis; and a light source for supplying light to the opposed end of said light waveguide, said light source being arranged to move with said opposed end of said light waveguide as said light waveguide is turned about said knife edge as axis.

4. A microtome apparatus according to claim 3 wherein the range of movement of said light source is limited such that, when the angle between the light waveguide and the vertical exceeds a predetermined value, the light source remains stationary as said angle is further increased, whereby light from said light source illuminates the surface of a specimen mounted in said specimen holder without passing through said light waveguide.

5. A microtome apparatus according to claim 3 wherein said light source comprises a light waveguide prism.

6. A microtome apparatus according to claim 3 further comprising a microscope disposed above the knife edge and on the opposed side of the vertical plane containing the knife edge from the specimen holder, said microscope being arranged to form an image of the slit lying between said knife edge and a specimen mounted in said specimen holder when said knife edge lies closely adjacent said mounted specimen.

* * * * *